(12) United States Patent
Heath et al.

(10) Patent No.: US 6,224,890 B1
(45) Date of Patent: May 1, 2001

(54) 3-ALKYL-1-BUTANOL ATTRACTANTS FOR FRUGIVOROUS PEST INSECTS

(75) Inventors: Robert R. Heath; Nancy D. Epsky, both of Gainesville, FL (US)

(73) Assignee: The United States of Americas as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/156,625

(22) Filed: Sep. 18, 1998

(51) Int. Cl.[7] .................................................. A01N 25/08
(52) U.S. Cl. ........................... 424/409; 424/405; 424/84; 514/554; 514/557; 514/663; 514/724; 43/107
(58) Field of Search .............................. 424/405, 84, 409, 424/411; 43/407; 514/554, 557, 663, 724

(56) References Cited

U.S. PATENT DOCUMENTS

| 4,160,824 | * | 7/1979 | Inazuka et al. | 424/84 |
| 5,656,260 | | 8/1997 | Boden et al. | 424/405 |
| 5,766,617 | | 6/1998 | Heath et al. | 424/410 |

OTHER PUBLICATIONS

M. McPhail, *Journal of Economic Entomology*, vol. 32(6), pp. 758–761, (1939).
Nakagawa et al., *Journal of Economic Entomology*, vol. 63(1), pp. 227–229, (1970).
Leonhardt et al., *American Chemical Society*, pp. 159–173, (1982).
W. Newell, *Journal of Economic Entomology*, vol. 29(1), pp. 116–120, (1936).
Nout et al., *Journal of Chemical Ecology*, vol. 24(7), pp. 1217–1239, (1998).
Bateman et al., *Aust. J. Agric Res.*, vol. 32, pp. 883–903, (1981).
Buttery et al., *J. Agri. Food Chem.*, vol. 31(4), pp. 690–692, (1983).
Christenson et al., "Biology of Fruit Flies", pp. 171–192.
DeMilo et al., *J. Agric. Food Chem.*, vol. 44, pp. 607–612, (1996).
Heath et al., *Florida Entomologist*, vol. 79(2), pp. 144–153, (1996).
Heath et al., *Florida Entomologist*, vol. 79(1), pp. 37–48, (1996).
Lee et al., *J. Agric. Food Chem.*, vol. 43, pp. 1348–1351, (1995).
Robacker et al., *Journal of Chemical Ecology*, vol. 16(10), pp. 2799–2815, (1990).
Robacker et al., *Annals of the Entomological Society of America*, vol. 84(5), pp. 555–559, (1991).
Robacker, D., *Enviromental Entomology*, vol. 20(6), pp. 1680–1686, (1991).

(List continued on next page.)

*Primary Examiner*—Neil S. Levy
(74) *Attorney, Agent, or Firm*—M. Howard Silverstein; John D. Fado; G. Byron Stover

(57) ABSTRACT

Compositions and lures are described which provide 3-alkyl-1-butanol vapors and vapor blends of 3-alkyl-1-butanol with one or more compounds selected from the group consisting of acetic acid, ammonia, putrescine and mixtures which function as highly effective attractants for frugivorous pest flies especially of Anastrepha species. By attracting frugivorous pest insects, the chemical attractants provide means for detecting, surveying, monitoring and/or controlling the pest fruit flies.

16 Claims, 4 Drawing Sheets

OTHER PUBLICATIONS

Robacker et al., *Enviromental Entomology*, vol. 22(6), pp. 1367–1374, (1993).
Robacker et al., *Journal of Chemical Ecology*, vol. 19(3), pp. 543–557, (1993).
Robacker et al., *Journal of Chemical Ecology*, vol. 22(3), pp. 499–511, (1996).
Robacker et al., *Journal of Chemical Ecology*, vol. 19(12), pp. 2999–3016, (1993).
Greany et al., *Ent. Exp. & Appl.*, vol. 21, pp. 63–70, (1977).
SAS/STAT User's Guide, "The GLM Procedure", Chapter 20, pp. 551–555, Release 6.03 Edition.

U.S. patent application No. 09/041, 056, Landolt et al., "Chemical Attractants for Yellowjackets and Paper Wasps", filed Mar. 10, 1998.
U.S.D.A. Docket No. 0166.98, Landolt and Heath, "Chemical Attractants for Moths", filed concurrently herewith.
C. Lauzon, *Environmental Entomology*, vol. 27(4), pp. 853–857, (1998).
1997 Annual Report, USDA,ARS, Gainesville, FL, (Jan. 1998).
DeMilo et al., *Journal Agric. Food Chem.*, vol. 44, pp. 607–612, 1996.*

* cited by examiner

3-ALKYL-1-BUTANOL ATTRACTANTS FOR FRUGIVOROUS PEST INSECTS

BACKGROUND OF THE INVENTION

1. Field of the Invention

The present invention relates to synthetic insect attractant compositions. More particularly, the invention relates to chemical attractant compositions and use thereof to detect, survey, monitor, and/or control frugivorous pest insects such as Anastrepha species, more particularly *Anastrepha ludens* (Loew), *Anastrepha suspensa* (Loew).

2. Description of the Art

Control of frugivorous pest flies is of considerable economic importance for fruit and vegetable production and export. Quarantine and regulatory agents expend substantial efforts to detect newly introduced species of economically important fruit flies. The Mexican fruit fly, *Anastrepha ludens* (Loew) is a frugivorous tephritid ranging from southern Texas to at least Costa Rica (Stone, The Fruit flies of the genus Anastrepha, U.S. Department of Agriculture Misc. Publ. 439, 1942). This fly is one of the most polyphagous of the approximately 180 species of the genus Anastrepha, known in the field from at least 36 species of hosts in 14 plant families (Norrbom and Kim, A list of the reported host plants of species of Anastrepha (Diptera:Tephritidae), U.S. Department of Agric. Animal Plant Health Insp. Serv., APHIS 81–52:114 p., 1988). Its affinity for citrus has made it one of the most economically important insects in citrus-growing regions all over the world. This is especially true where it does not occur naturally, but where accidental introduction could cause an economic catastrophe to the citrus industry. Even a small infestation makes all fruit grown in the area suspect and thus unsalable to many would-be importing countries without costly post-harvest treatments or radical extermination programs. Because of this threat, much emphasis has been placed on detection of this species before its populations can become well established and thus difficult to eradicate. The Caribbean fruit fly, *Anastrepha suspensa* (Loew), is known to infest over 80 species of fruit. The presence of the Caribbean fruit fly in Florida posses a constant threat to other citrus growing regions.

Much emphasis has been placed on detection and eradication of frugivorous pest flies. The development of improved lures is needed to monitor and suppress populations of this and other pest fruit flies and to prevent establishment of populations in areas that are currently without these pests.

Methods developed for monitoring, controlling, and eradicating frugivorous fruit flies (Tephritidae) have relied extensively on the use of chemical attractants. Methyl eugenol plus dibrom; cuelure plus dibrom; ammonium salts; and a mixture of 1,7-dioxasprio[5,5]undecane with α-pinene or n-nonanal; and spiroacetal are used as lures for species of Dacus. A composition of hexyl acetate, (E)-2-hexen-lyl acetate, butyl 2-methylbutanoate, propyl hexanoate, hexyl propanoate, butyl hexanoate, and hexyl butanoate is used as a lure for species of Rhagoletis. Effective insect-detection systems are essential for preventing the establishment of fruit flies and surveys for these flies are included in state and federal exotic pest-detection programs in at least nine southern and southwestern states (Lance and Gates, J. Econ. Entomol., Volume 87, 1377–1383, 1994). Califormia, Texas, and Florida maintain large number of trimedlure-baited Jackson traps ((Harris et al., J. Econ. Entomol., Volume 64, 62–65, 1971) for the detection of male *C. capitata* and aqueous protein-baited McPhail traps (Newwll, J. Econ. Entomol., Volume 29, 116–120, 1936; McPhail, J. Econ. Entomol., Volume 32, 758–761, 1939) for detection of male and female *C. capitata* (Mediterranean fruit fly) and *A. ludens* (USDA, National exotic fruit fly trapping protocol, Animal and Plant Health Inspection Service, Plant Protection and Quarantine, Hyattsville, Md., 1991). McPhail traps are currently used for monitoring fruit flies throughout fruit growing areas of the world. There are several problems associated with use of either of these trapping systems. Although trimedlure is effective in attracting male Mediterranean fruit flies, it is either only weakly active in attracting or is completely ineffective in attracting female Mediterranean fruit flies (Nakagawa et al., J. of Econ. Entomol., Volume 63, 227–229, 1970). Inability to capture female *C. capitata* limits the effectiveness of trimedlure-baited traps as a control device and no information on population dynamics of the female flies is obtained. McPhail traps, bell-shaped glass traps with a water reservoir containing aqueous protein baits, offer the advantage of attracting both male and female *C. capitata* and *A. ludens* fruit flies. However, these traps are cumbersome and have numerous disadvantages of their own. Servicing the trap requires that water and bait be added in a somewhat maladroit manner in which the trap is turned upside down, bait added and then the trap returned to an upright position. This process often results in bait spillage, and the spilled bait becomes a food source for flies outside the trap. Removal of insects trapped requires considerable effort. The contents of the trap must be filtered through a screen to separate the insects from the bait solution. Trapped fruit flies are often found severely decomposed with parts missing. Thus, when these traps are used in conjunction with marked flies in sterile release programs difficulty is encountered in determining whether a trapped fly is a sterile or a wild fly. Other factors that contribute to the difficulty in the deployment of McPhail traps include the size and weight of the trap, and the fragile nature of glass. Protein baits also attract a number of non-targeted insects and considerable time is required to sort among the trapped insects.

Conventional lures currently used to survey and detect frugivorous pests are protein baits such as fermenting yeast hydrolysate (Greany et al., Ent. exp & Appl. 21:63–70, 1977) and protein hydrosylate (McPhail, J. Econ. Entomol. 32:758–761, 1939). The problem with protein lures is that they capture large numbers of nontarget insects. Furthermore, the only lures that are available for attracting both female and male fruit flies are protein baits.

Adult fruit flies require sugar to survive (Christenson & Foote, Annual Review of Entomology 5:171–192, 1960), and honeydew secreted by homopterous insects is recognized as an important food source for adult tephritids (Christenson et al., Annual Review of Entomology 5:171–192, 1960). Female fruit flies also require protein to ensure fecundity, and this protein requirement is the primary basis for traps for detection of female fruit flies.

Hundreds of compounds are known to be released from protein baits (Morton & Bateman, Aust. J. Agric. Res. 32:905–916, 1981). Examples of some volatile components of commercial hydrolyzed protein insect baits are phenylacetaldehyde, acetic acid, furfuryl alcohol, 2-acetylfuran, benzaldehyde, methanol, 2-acetylpyirole, furfural, 5-methyl-2-phenyl-2-hexenal, 5-methyl-2-[(methylthio)methyl]-2-hexenal and ammonia. Ammonia (Bateman & Morton, Aust. J. Agric. Res. 32:883–903, 1981; Mazor et al., Entomol. Exp. Appl. 43:25–29, 1987), acetic acid (Keiser et al., Lloydia 38: 141–152, 1976), and various other volatiles (Buttery et al., J. Agric. Food Chem. 31:

689–692, 1983) have been investigated as attractants for fruit flies. These reports, however, do not provide information regarding released amounts or ratios of the compounds tested or the effectiveness of these chemicals as compared to McPhail traps.

Bacteria in the family Enterobacteriaceae have been found in association with tephritid fruit flies (e.g., Rubio and McFadden, Annu. Entomolo. Soc. Amer., Volume 59, 1015–1016, 1966; Boush et al., Environ. Entomol., Volume 1, 30–33, 1972; Rossiter et al., In R. Cavallora (ed.), Fruit Flies of Economic Importance, A. A. Balkema, Rotterdam, 77–82, 1982; MacCollom and Rutkowski, In Proceedings, Second International Symposium on Fruit Flies, Crete, Greece, 251–253, 1986; Jang and Nishima, Environ. Entomol., Volume 19, 1726–1731, 1990) and bacteria in this family may be strongly attractive to fruit flies (Drew and Lloyd, In A. S. Robinson and G. Hooper (eds.), World Crop Pests, Volume 3A, Fruit Flies Their Biology, Natural Enemies and Control, Elsevier, N.Y., 131–140, 1989; Martinez et al., Florida Entomol., Volume 77, 117–126, 1994). Bacteria on plant surfaces may serve as a protein source for adult tephritids in nature (Drew et al., Oecologia (Berlin), Volume 60, 279–284, 1983). Drew and Fay (J. Plant Prot. Tropics, Volume 5, 127–130, 1988) hypothesized that increased capture of Bactrocera tryoni (Froggatt) in liquid protein bait with bacteria was due to volatile metabolites produced by bacterial growth. Davis et al. (J. Agric. Entomol., Volume 1, 236–248, 1984) demonstrated that there was greater attraction of Caribbean fruit flies, *Anastrepha suspensa* (Loew), to liquid protein bait solution in McPhail traps versus liquid protein bait placed on cotton wicks in Jackson traps and speculated that this was due in part to volatile end products from microbial breakdown that occurred in the McPhail traps.

Several studies have evaluated the attractiveness of various bacteria that were found in association with tephritids. Jang and Nishijima (1990, supra) isolated 14 bacterial species from wild and laboratory-reared oriental fruit flies, Batrocera dordalis Hendel, and most of these bacteria belonged to the family Enterobacteriaceae. They found that several bacterial species were more attractive to female than to male flies and that washed cells, that is cells that were separated from the growth media, were more attractive than water or phosphate buffer. Several strains of *Staphylococcus aureus* were found to be attractive to adults of the Mexican fruit fly, *Anastrepha ludens* (Loew)(Robacker et al., Annu. Entomol. Soc. Amer., Volume 84, 555–559, 1991). Attraction to bacterial odors was mediated by feeding history of the flies, as response to bacterial odors decreased with increased sugar hunger (Robacker and Garcia, Environ. Entomol., Volume 22, 1367–1374, 1993) and increased with increased protein hunger (Robacker and Moreno, Florida Entomol., Volume 78, 62–69, 1995). Ammonia, which is known to be the primary fruit fly attractant that is emitted from liquid protein baits (Bateman and Morton, Australian J. Agric. Res., Volume 32, 883–903, 1981; Mazor et al, Entomol.Exp. Appl., Volume 43, 25–29, 1987), is produced by microbial growth (e.g., Howell et al., Phytopathol., Volume 78, 1075–1078, 1988; Scrapati et al, J. Chem. Ecol., Volume 22, 1027–1036, 1996). Several volatile chemicals have been identified from headspace analysis of bacteria and/or culture media (Robacker et al., J. Chem. Ecol., Volume 19, 543–557, 1993; Lee et al., J. Agric. Food Chem., Volume 43, 1348–1351, 1995; DeMilo et al., J. Agric. Food Chem., Volume 44, 607–612, 1996), although Robacker and Flath (J. Chem. Ecol., Volume 21, 1861–1874, 1995) could not determine if the chemicals that were biologically active in laboratory bioassays were produced by the bacteria or were an artifact of the analytical procedure. 3-Methyl-1-butanol has been identified previously from fruit fly attractive substances. It was one of 28 chemicals identified as volatiles emitted from fermented host fruit for *A. ludens* (Robacker et al, J. Chem. Ecol., Volume 16, 2799–2815, 1990). It was not attractive by itself, and it was removed from further consideration as a host fruit attractant volatile. Research of volatiles from bacteria indicated that 3-methyl-1-butanol was the major volatile obtained from autoclaved supernatant of 8-day old cultures of Klebsiella pneumoniae-inoculated TSB (Lee et al, 1995, supra) and of 4- and 8-day old cultures of *Citrobacter freundii*-inoculated TSB (DeMilo et al, 1996, supra). There were 20 and 21 chemical components, respectively, identified in addition to this compound. However, there was no information regarding the attractiveness of the individual chemicals. In comparisons of autoclaved supernatant to non-autoclaved supernatant of 4-day old *C. freundii*-inoculated TSB, the amount of 3-methyl-1-butanol was greatly reduced in the autoclaved supernatant with no corresponding change in *A. ludens* attraction in laboratory bioassays (DeMilo et al., 1996, supra). 3-Methyl-1-butanol was identified as a minor component in vacuum steam distillation extraction of corn protein hydrolyzate bait (Buttery et al., J. Agric. Food Chem., Volume 31, 689–692, 1983). Thus, it is not known if there are volatile chemicals in addition to ammonia produced by actively growing bacteria that are attractive to fruit flies.

Enterobacter agglomerans is one of several Enterobacteriaceae that have been isolated from adults of the apple maggot, *Rhagoletis pomonella* (Walsh), and from apple maggot-infested fruit (MacCollom et al, J. Econ. Entomol., Volume 85, 83–87, 1992). Washed cell preparations of an apple maggot-associated isolate of *E. agglomerans* were attractive to foraging adults in field trails while washed cells of *Klebsiella ozytoca, Enterobacter cloacae, Psuedomonas fluorescens*, and *Bacillus cereus* captured less flies than *E. agglomeran* cells (MacCollom et al., 1992, supra). Recently, Lauzon et al. (Environ. Entomol., Volume 27 (4), 853–857, 1998) demonstrated that culture plates inoculated with *E. agglomerans* are attractive to apple maggot flies in laboratory bioassays. However, variation in fruit fly attraction may occur within species as Lauzon et al. found *E. agglomerans* isolates from different sources varied in ability to attract apple maggot flies and that attraction may be related to the substrates which the isolates are growing (Lauzon et al., J. Chem. Ecol., 1998(b), in press). This bacterium has been isolated from adults, larvae and fruit infested with larvae of the Caribbean fruit fly, *Anastrepha suspensa* (Loew), field collected in south Florida (C. R. L., unpublished data). While various attractant compositions are known in the art, there remains a need in the art for highly effective attractant compositions to improve monitoring and controlling of frugivorous pest insects, especially those of the genus Anastrepha. The present invention provides a composition and method of use which is different from related art attractant compositions.

SUMMARY OF THE INVENTION

It is, therefore, an object of the present invention to provide a system for monitoring and/or controlling frugivorous pest insects using an attractant lure which provides an attractant vapor of 3-alkyl-1-butanol for attracting frugivorous pest flies.

A further object of the present invention is to provide a system for monitoring and/or controlling frugivorous pest insects using an attractant lure which provides attractant vapor blends of chemical stimuli with a synergistic amount of a 3-alkyl-1-butanol.

Another object of the present invention is to provide an attractant which provides vapor blends of ammonia, acetic acid, or putrescine (1,4-diaminobutane), and 3-alkyl-1-butanol for attracting frugivorous pest flies.

Still another object of the present invention is to provide a chemical attractant made up of ammonium acetate, putrescine, and 3-alkyl-1-butanol which provides vapor blends of ammonia, acetic acid, putrescine and 3-alkyl-1-butanol for attracting frugivorous pest flies.

A still further object of the present invention is to provide a system for monitoring and/or controlling frugivorous pest insects using an attractant lure which provides an attractant vapor of 3-methyl-1-butanol for attracting frugivorous pest insects.

Another object of the present invention is to provide a system for monitoring and/or controlling frugivorous pest insects using an attractant lure which provides attractant vapor blends of chemical stimuli with a synergistic amount of 3-methyl-1-butanol.

A still further object of the present invention is to provide an attractant which provides vapor blends of ammonia, acetic acid, or putrescine and 3-methyl-1-butanol for attracting frugivorous pest flies.

Another object of the present invention is to provide a chemical attractant made up of ammonium acetate, putrescine, and 3-methyl-1-butanol which provides vapor blends of ammonia, acetic acid, putrescine and 3-methyl-1-butanol.

Further objects and advantages of the invention will become apparent from the following description.

DETAILED DESCRIPTION THE INVENTION

Figure 1:
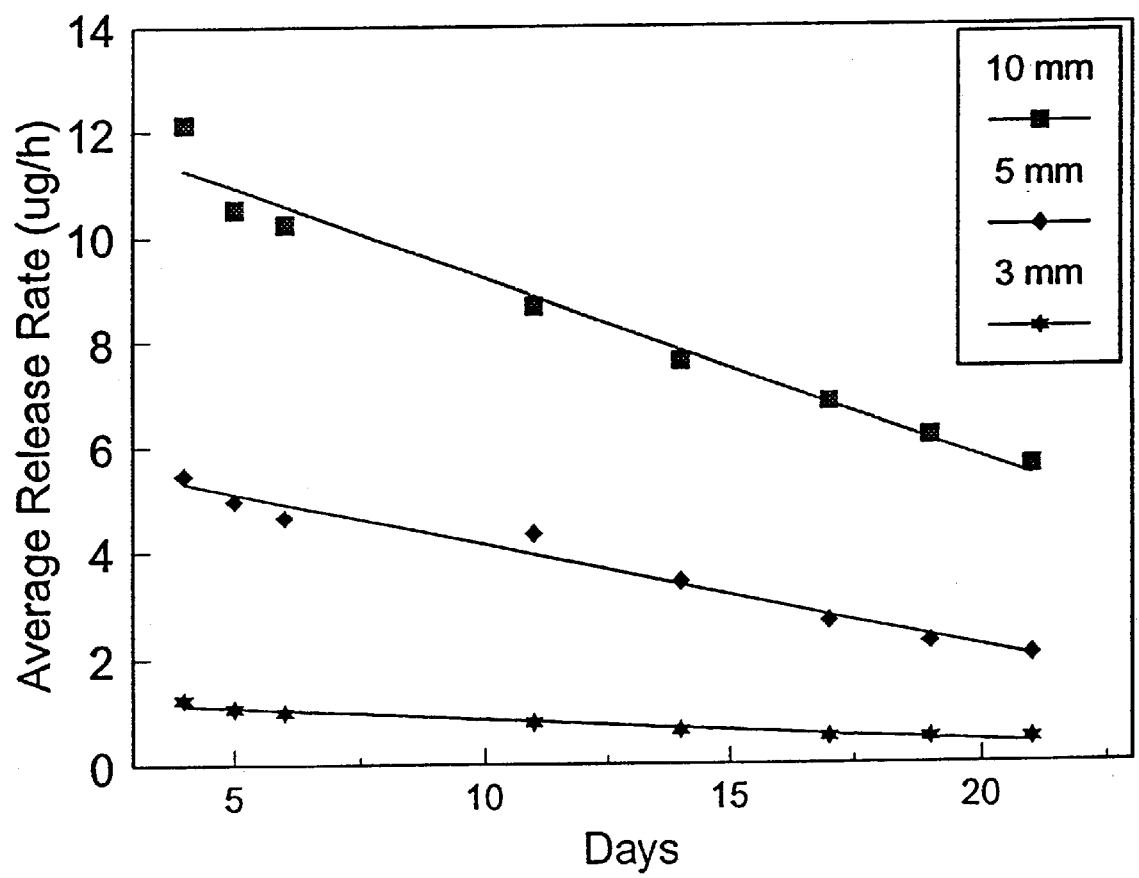
FIG. 1 is a graph showing average release rates ($\mu$g per hour) over time of 3-methyl-1-butanol formulated in membrane-based lures. Regressions were determined from lures (N=2) containing about 50 $\mu$l of 3-methyl-1-butanol and with membrane release areas of about 3-(solid line, star), 5-(solid line, diamond), and 10-mm (solid line, square).

The invention provides an attractant system for monitoring and/or controlling frugivorous pest flies without using aqueous protein solutions. The method of the invention incorporates a unique chemical stimuli attractant. It also includes unique combination of chemical stimuli including a synergist which attract fruit flies. The synthetic attractant of the present invention comprises 3-alkyl-1-butanol, preferably 3-methyl-1-butanol. The synthetic attractant composition of the present invention also comprises a vapor blend or vapor mixture of acetic acid, ammonia, or putrescine with 3-alkyl-1-butanol, especially 3-methyl-1-butanol. The synthetic attractant composition of the present invention further comprises a vapor blend or vapor mixture of acetic acid, ammonia, putrescine and 3-alkyl-1-butanol, especially 3-methyl-1-butanol.

A lure is made up of chemicals of the above defined attractant compositions which provide a vapor or vapor blend which is highly attractive to the capture of Anastrepha species, especially *Anastrepha ludens* (Loew) and *Anastrepha suspensa* (Loew).

Although it is known that numerous chemicals are released from protein baits the attractiveness of some of these chemicals released at various doses was heretofore unknown. Specifically, although ammonia has been suggested as an attractive chemical for many fruit flies, only moderate attractiveness to, for example, the Mediterranean fruit fly has been observed (Baker et al., Journal of Economic Entomology 83: 2235–2245, 1990). Although a commercial formulation containing ammonium acetate is available that will release ammonia, no reliable quantitative data is available regarding the release rate of ammonia from this formulation. Furthermore, methods to vary the release rate of this formulation heretofore were undescribed. We have discovered that a blend of ammonia, acetic acid (from an ammonium acetate formulation) and putrescine is needed for attraction of fruit flies. The addition of a 3-alkyl-1-butanol, especially 3-methyl-1-butanol, significantly increases the attractiveness of the ammonia vapor alone, or ammonia, acetic acid and putrescine vapor blend. For purposes of the present invention, chemical stimuli includes ammonia, acetic acid, putrescine (1,4-diaminobutane) or 3-alkyl-1-butanol, especially 3-methyl-1-butanol. An effective amount of each of these compounds is defined as that amount of each of these compounds that provides a release rate of the compound or blend that attracts fruit flies to the location containing the stimuli at a rate significantly higher than flies are attracted to a location where the stimuli is absent.

A synergist for the chemical stimuli is defined as any 3-alkyl-1-butanol that significantly increases the attractiveness of the chemical stimuli as defined above. 3-alkyl-1-butanol is preferred and 3-methyl-1-butanol (isoamyl or isopentyl alcohol) is most preferred as a synergist. A synergistic amount, effective amount, or synergistically effective amount is defined as that quantity of a 3-alkyl-1-butanol that significantly increases attraction of fruit flies to a location that contains the above defined chemical stimuli at a rate significantly higher than the rate flies are attracted to a location containing the stimuli alone.

All compounds for producing the vapor composition of the invention are commercially available. Acetic acid vapor is provided by compounds that produce volatilized acetic acid, for example, aqueous acetic acid, glacial acetic acid, glacial (concentrated) acetic acid, or ammonium acetate. Ammonia vapor is provided by compounds that produce volatilized ammonia, for example, ammonium carbonate, ammonium bicarbonate, ammonium acetate, etc. Ammonium acetate is most preferred for providing acetic acid and ammonia vapors. 3-alkyl-1-butanol vapors are provided by the compound 3-alkyl-1-butanol, especially 3-methyl-1-butanol.

It is envisioned that the chemical attractants of the invention would be useful in detecting, surveying, monitoring and/or controlling frugivorous pest insects, especially *Anastrepha ludens* (Loew) and *Anastrepha suspensa* (Loew) when used as a lure. A lure includes a dispenser means which contains a chemical or chemicals of the attractant compositions of the present invention which provide the attractant vapor or vapor blend. For purposes of this invention, a dispenser means is defined as any means which both (a) contains or holds unvolatilized compound or compounds used to produce the vapor or vapor blend of the present invention; and (b) releases the compound or compounds in the vapor phase to form the vapor or vapor blend.

A dispensing means may take several forms. Adsorbent material such as cotton or paper which holds and releases the chemical stimuli and synergist may be used., In general, a dispensing means will comprise a reservoir for holding an amount of a compound either within a space or a polymeric matrix, with the release into the atmosphere controlled by a permeable wall or membrane or by a small opening surrounded by an impermeable wall or membrane. Examples of dispensers are detailed in the examples that follow. Examples include a release membrane made from, for example, polyethylene, polypropylene, polyvinlychloride, Mylar, and acrylic as described in Leonhardt et al (Insect Pheromone Technology: Chemistry and Applications, ACS Symposium Series 190, 1982; herein incorporated by reference) and Kydonisus (Controlled Release Pesticides, ACS Symposium Series 53, 1977; herein incorporated by reference). For ammonia and acetic acid, a commercially available preparation of ammonium acetate from a release membrane called BioLure® (Consep Inc., Bend, Oreg.) can also be used. Ammonium acetate in a release membrane called Biolure® (Consep Inc., Bend, Oreg.) is preferred for the composition comprising ammonia, acetic acid, putrescine and 3-alkyl-1-butanol of the present invention. The amount of ammonia and acetic acid is quantified as described in U.S. Pat. No. 5,766,617 (Heath and Epsky, Jun. 16, 1998; herein incorporated by reference in its entirety). Capillary tubes and vials can also be used for some of the compounds used in the present invention.

A preferred release rate range for ammonia is approximately about 40 $\mu$g/hr to about 600 $\mu$g/hr. A more preferred range of release is about 45 to 400 $\mu$g/hr. A most preferred release rate is approximately 100 or 300 $\mu$g/hr of ammonium (Heath et al, Econ. Entomol., Volume 88, 1307–1315, 1995; U.S. patent application Ser. No. 08/647,211, filed May 09, 1996 which is a file wrapper continuation of patent application Ser. No. 08/231,213, filed Apr. 22, 1994, now abandoned; and Ser. No. 08/440,023, a divisional of Ser. No. 08/231,213, filed May 12, 1995; all herein incorporated by reference). A preferred release rate for acetic acid is approximately leg/hr to approximately 16 $\mu$g/hr. A more preferred range of release is 1.5 to 13 $\mu$g/hr. A most preferred release rate is approximately 4 $\mu$g/hr of acetic acid (Heath et al., 1995, supra).

Putrescine lures are prepared using a polyethylene membrane system previously described (Epsky et al., Environ. Entomol., Volume 24, 1387–1395, 1995; herein incorporated by reference). It can also be placed in a vial as substantially pure liquid preparation (neat). A preferred range for putrescine is approximately 25–300 $\mu$l of a substantially pure liquid preparation. A more preferred range is approximately 50 to 200 $\mu$l of putrescine. A most preferred amount is approximately 50 $\mu$l.

The 3-alkyl-1-butanol lure was formulated using approximately a 3×5 cm lure prepared by folding a 6×5 cm piece of about 6 mil impermeable polyethylene (backing) in half. An approximately 1.17 cm diameter hole was cut into about the center of the front of the lure and a piece of 1 mil high density polyethylene (membrane) film (Consep Inc., Bend. Oreg.) was placed inside the lure. The bottom and sides were heat sealed to form an envelope and to secure the membrane. The release area of the membrane was reduced to about a 10 mm diameter circle by placing a piece of aluminum tape over the about 1.17 cm hole in the front of the lure. Lures contained filter paper and a plastic grid to provide mechanical stability. A preferred range of release rates for 3-alkyl-1-butanol from the lure is approximately 1 to 20 $\mu$g/hour. A more preferred release rate range is approximately 1–12 $\mu$g/hour. A most preferred release rate is approximately 8 or 12 $\mu$g/hr.

The lures may be combined with feeding stimulants to provide baits for frugivorous pest flies. Toxicants may also be added to produce poisoned baits. See U.S. patent application Ser. Nos. 08/647,211 and 08/440,023; and U.S. Pat. No. 5,766,617; cited supra. Other compounds and materials may be added to a formulation, lure, bait or trap provided they do not substantially interfere with the attractancy of the attractant vapor composition of the invention. Whether or not an additive substantially interferes with the attractant activity can be determined by standard test formats, involving direct comparisons of efficacy of the vapor or vapor blends of the present invention without an added compound and the vapor or vapor blends of the present invention with an added compound. Reductions in attractancy, such as reduced capture of fruit flies in traps baited with the attractant plus additive, may be determined with standard statistical analyses.

The attractants of the present invention may be used as detecting agents, surveying agents, monitoring agents, or control agents for frugivorous pest insects. Conveniently, the attractants are dispensed within trapping means to attract and trap fruit flies. A trapping system for monitoring or controlling fruit flies includes trapping means, and a dispenser means located within the trapping means which provides an effective attractant amount of a vapor or vapor blends of the attractants of the present invention. A trapping means is any device for catching insects, particularly frugivorous pest insects. These include for example, the fruit fly trap described in U.S. patent application Ser. Nos. 08/647, 211 and 08/440,023; and U.S. Pat. No. 5,766,617; cited supra or a sticky cylindrical trap. The compounds that produce the attractant vapor or vapor blends may be presented as a mixture or in separate dispenser(s) within the trap as described above.

Insecticides or toxicants for frugivorous pest insects includes methomyl (E.I. DuPont De Nemours and Co., Newark, Del.; 98% [AI]), Malathion, dichlorvos and naled. Other toxicants are selected from the group consisting of organophosphorus toxicants, carbamates, inorganic toxicants, and insect growth regulators. The toxicant may be in powdered form or incorporated into a bait whereby the flies are attracted to the toxicant and becomes contaminated or infected (in the case of pathogens) with the toxicant.

Toxicants which may be useful in this invention are those which will not adversely affect the attractiveness of the attractants of the invention. A variety of matrix materials may also be employed as a carrier for the toxicant. See for example U.S. patent application Ser. Nos. 08/647,211 and 08/440,023, supra which describes toxicant panels containing a feeding stimulant useful in frugivorous pest insect traps.

The invention is also directed to kits. In one aspect the kit includes a trap and a lure for use within the trap and which provides the attractant vapor or vapor blends. Another kit includes components of the attractant vapor blend wherein one component is ammonium acetate, another component is putrescine and a third component is 3-alkyl-1-butanol and means for dispensing each of the components to provide the attractant blend of the invention.

The kit may also include a toxicant bait in a matrix or suitable carrier for frugivorous pest insects. The bait may also contain additives, such as feeding stimulants, toxicants, extenders, antioxidants and/or UV adsorbers.

The invention is also directed to a packaged attractant which comprises at least a 3-alkyl-1-butanol, especially 3-methyl-1-butanol. It can also comprise at least three components wherein one component is ammonium acetate which provides acetic acid vapor and ammonia vapor, a second component is putrescine which provides putrescine vapor, and a third component is a synergist 3-alkyl-1-butanol which provides 3-alkyl-1-butanol vapor, especially 3-methyl-1-butanol; wherein the components are packaged in separate containers and wherein the packaged attractant or attractant plus synergist further comprises instructions for producing a volatilized blend of the component(s) when the component(s) is/are released from the container(s).

Factors such as insect population density, age-structure of the target population, temperature, wind velocity, and release rate will influence the response of the flies and thus the actual number of flies trapped. Factors such as temperature, wind velocity and release substrate will influence chemical release rate. The amount of compound in a particular set of circumstances that will provide a release rate within the effective range can readily be determined by a dose response field test as previously described in the U.S. patent applications cited supra.

Uses of the Invention.

The invention is used as a monitoring, control, and/or detection tool for frugivorous pest insects such as *Anastrepha ludens* (Loew) and *Anastrepha suspensa* (Loew), for example. One method is to deploy a trap containing the attractant of the invention and tabulate the catch to determine size and location of fruit fly infestation. Economic use of appropriate pest management systems can then be determined.

The invention is used in combination with insecticide application or other control measures. The invention is used to attract flies and to induce them to enter a trap where they contact an effective amount of toxicant to achieve control. An effective amount of the toxicant is an amount that is lethal for an exposed insect or at least sublethal but sufficient to incapacitate the insect in regard to future mating or oviposition activity. Illustrative of the wide variety of toxicants which may be used with the invention are, for example, methomyl, malathion, dichlorvos and naled or a combination of two or more.

Another method is for control of fruit flies by using the invention to detect the location and boundaries of localized fruit fly infestations and employ in the area chemosterilants, bioregulator agents, parasites, predators or other biological control agents for fruit flies.

EXAMPLES

The following examples illustrate the use of the invention for the control of frugivorous pest insects using the Mexican and Caribbean fruit flies as a test model. They are intended to further illustrate the invention and are not intended to limit the scope of the invention as defined by the claims.

Example 1

Stock cultures of *Enterobacter agglomerans*, maintained in Amherst, Mass., were plated on tryptic soy agar (TSA; Difco Laboratories, Detroit, Mich.) in early log phase and sent via overnight delivery to our laboratory. Sterile TSA plates were included as controls. Fresh cultures were shipped periodically to the lab and samples of cells subcultured in our lab were shipped back to Amherst for confirmation of culture purity. Upon receipt, plates were left at room temperature overnight to ensure a minimum of 24 hours of growth. Growth of colonies on the plates prior to arrival in our lab was affected by ambient temperatures during shipment, so there was variation in the amount of growth that occurred before the plates arrived in Gainesville. Therefore, for comparative purposes, chemical analyses were conducted on plates allowed to grow an additional 24 hours to determine if further growth affected quantitative release of volatile chemicals. After about 24 or 48 hours of growth, plates were tested immediately or were placed in a refrigerator at about 7° C. until use. Plates removed from the refrigerator were held at room temperature for at least 1 hour, and plates were used within 1 week of receipt. For studies that tested washed cells, cells were scraped off the TSA and were subcultured in tryptic soy broth at about 25° C. The *E. agglomerans* was propagated by inoculating one loopful (approximately 3-mm diameter) of an about 24 hour subculture into test tubes containing about 10 ml TSB and incubating for about 24 hour at about 25° C. The cells were separated from the culture media by centrifugation for about 10 minutes at approximately 17,000×G (about 0° C.) and the TSB supernatant was discarded (MacCollom et al., 1992, supra). Cells were washed and concentrated by resuspending the pellet in sterile water (deionized), combining samples and centrifuging again to remove residual media from the cells. This process was repeated twice. The final pellet from about 40 ml of subculture was resuspended in approximately 10 ml of sterile water to obtain about a four fold increase in concentration.

Example 2

Caribbean fruit flies, *Anastrepha suspensa*, (Loew)) were obtained as pupae from the Florida Department of Agriculture and Consumer Services, Division of Plant Industry. Flies were maintained as previously reported (Epsky et al., Florida Entomol., Volume 76, 626–635, 1993; herein incorporated by reference). Females that were about 4–12 days post eclosion were used for all trails. Fully fed flies were used for all bioassays to reduce biased attraction to ammonia, which is enhanced by subjecting flies to protein starvation prior to testing (Robacker, Environ. Entomol., Volume 20, 1680–1686, 1991).

Example 3

Capillary gas chromatography (CGC) analyses were conducted to identify and quantify the volatile chemicals from *E. agglomerans*. Head space volatiles were collected for about 1 hour at about 1 liter/minute airflow using purified air and were analyzed using collection systems described previously (Heath and Manukian,(J. Chem. Ecol., Volume 18, 1209–1226, 1992; Heath et al, Heath et al., J. Chem. Ecol., Volume 19, 2395–2410, 1993; herein incorporated by reference). Initially, volatile collections were made from washed cells (about 20 ml), TSB supernatant (about 20 ml) and sterile TSB (about 40 ml). The amount of volatile chemicals released from washed cells was too low to analyze by CGC using standard on-column injection techniques. Therefore, volatiles were introduced into the CGC using thermal desorbtion injection. For thermal desorbtion, volatiles were collected in 6-mm OD by 120-mm long Pyrex tubes packed with 15-mm bed length of adsorbent (Tenax TA 6/80 mesh) and were thermally desorbed using a Tekmar cryo-focusing automatic desorber onto a 30 m by 0.25 M methyl silicone capillary column interfaced to a Finnigan ion trap detection system mass spectrometer. Volatiles were analyzed by electron impact and by chemical ionization using isobutane as the reagent gas. Standard on-column injection techniques were used for analyses of sterile and $E$. agglomerans-inoculated TSA plates using a Hewlett-Packard Model 5890A Series II gas chromatograph, equipped with a cool on-column capillary injector (septum injector) and flame ionization detector. Compound identity was done by using mass spectroscopy. Mass spectra were obtained using the capillary columns, operated as described above, coupled to a Finnigan ITDS mass spectrometer in either electron impact or chemical ionization mode. The reagent gas used for chemical ionization was isobutane.

The release rates of ammonia from washed cell preparations, sterile and $E$. agglomerans-inoculated TSA plates were determined using an ammonia-specific ion-selective electrochemical probe (Orion, Boston, Mass.). Test substrates were placed into wide-mouth Erlenmeyer flasks (500 ml). About a 13 ml volume of washed cells was added to about 87 ml tap water for testing. The TSA plates were cut into four sections to facilitate placement into the flask. Sections were removed individually from a Petri dish and placed inoculated side up around the bottom of the flask so that all sections were exposed to the air flow. The flask was purged for about 1 hour with an air flow of about 1 liter/minute, and volatiles were then directed to a sparge system that consisted of a gas dispersion tube (#7198 Ace Glass, Vineland, N.J.) placed in a graduated cylinder containing 100 ml of HCl solution (about 0.05N). After a collection, the ionic strength of the sample solution was adjusted using about 5M NaOH/0.05M disodium EDTA/ 10% methanol containing a color pH indicator. A standard ammonium calibration curve was prepared each day an analysis was done.

Analysis of volatiles from $E$. agglomerans found that a single major peak with a retention time of about 6.5 minutes was present in both washed cells and E. agglormerans-inoculated TSA plates. Integration of chemicals detected showed that this peak accounted for greater than about 85% of total chemicals detected. A library search (National Institutes of Standards and Technology Library, Gaithersburg, Md.) based on electron impact mass spectral data provided a significant match of the unknown with 3-methyl-1-butanol. Confirmation was provided by comparison with synthetic 3-methyl-1-butanol (Aldrich, St. Louis, Mo.). The chemical ionization mass spectra of natural and synthetic 3-methyl-1-butanol were identical. Based on these analyses, we concluded that the major peak was 3-methyl-1-butanol. This peak was also found in volatiles from the TSB supernatant from $E$. agglomerans culture, however, it was one of numerous peaks and was not the major peak. No 3-methyl-1-butanol was detected among volatiles form sterile TSB media.

No ammonia was detected from the washed cell preparations. The amount of 3-methyl-1-butanol from washed cell preparations was variable and the amounts observed ranged from about 50 to 200 picograms/hour (n=5). Because of the low amounts observed no attempt was made to quantify release of 3-methyl-1-butanol from washed cells. Chemical analysis indicated that very little ammonia (about 16.0 µg/hour, n=2) and no 3-methyl-1-butanol was released from sterile TSA plates. $E$. agglomerans-inoculated TSA plats, which contained actively growing colonies of bacteria, released about 332.9 µg/hour (n=10) ammonia and about 1.48 Ag/hour (n=4) 3-methyl-1-butanol after about 24 hours of growth. There was large variability in release rates of both chemicals among inoculated plates as ammonia and 3-methyl-1-butanol release rates ranged from about 54.8–684.4 and about 0.80–2.28 µg/hour, respectively. Ammonia and 3-methyl-1-butanol release rates from plates after about 48 hours of growth averaged about 895.0 and 2.48 µg/hour, respectively. No attempts were made to quantify bacterial growth on the TSA plates before chemical analysis, but variation in amount of growth that occurred before arrival in Gainesville apparently contributed to variation in release rates obtained from the inoculated plates.

Example 4

Ammonium carbonate was formulated to release approximately 100 µg/hour ammonia by packing approximately 20 mg into the bottom of a heat-sealed 200 µl glass capillary pipette (Becton, Dickinson and Co., Parsippany, N.J.). The 3-methyl-1-butanol was formulated using a membrane-based formulation system described previously (Heath et al., Fla. Entolmol., Volume 79, 37–48, 1996; herein incorporated by reference). Briefly, a lure (approximately 3×5 cm) with about a 1.17 cm diameter hole cut in the center of the front of the lure was prepared using 6 mil impermeable polyethylene. Release rate was governed using 1 mil high density polyethylene (membrane) film (Consep Inc., Bend, Oreg.) that was placed inside the lure. The release area of the membrane was reduced to about a 3-, 5-, or 10-mm diameter circle by placing a piece of aluminum tape (United Tape Company, Cumming, Ga.) over the about 1.17 cm hole in the front of the lure. Lures contained filter paper and a plastic grid to provide mechanical stability. Lures were loaded with about 5- or 10-µl (low dose) or about 50 µl (high dose) of 3-methyl-1-butanol. Lures were placed in a hood with about a 0.25 cm/second air flow for about 24 hours before use in a laboratory bioassay. Longevity was determined for lures loaded with the 50 µl of 3-methyl-1-butanol and with 3-,5- and 10-mm membrane release area. The release rates from two lures of each membrane release area were measured after about 4 days and then about every 3–4 days over about a 21 day period using the same methods as those used for TSA plates. Lures were kept in a hood between measurements at ambient temperature and with an air flow of approximately 0.2 meter/second. Differences in release rates over time were compared with a heterogeneity of slopes model using Proc GLM (SAS Institute (SAS Institute, SAS/STAT guide for personal computers, version 6 edition. SAS Institute, Cary, N.C., 1985). Mean release rates were used in linear regression analysis to determine the change in release rate over time and the half-life of each lure.

Initial release rates (mean ±SD) from the low dose 3-methyl-1-butanol lures (i.e., with about 3-mm membrane release areas) were about 0.05±0.007, 0.08±0.018, and 0.19±0.018 µg/hour for lures loaded with about 5-µl, 10 µl and for two 10-Al-loaded lures, respectively. These lures were used in the laboratory bioassay comparisons with washed cells. Initial release rates from the high dose lures (i.e., loaded with about 50 μl) were about 1.23±0.30, 5.44±0.78, and 12.16±2.76 μg/hour for lures with about 3-, 5-, and 10-mm diameter membrane release areas, respectively. There were significant differences in both the y intercepts (F=156.14; df=2,42; P=0.0001) and the slopes of the regressions (F=31.55; df=2,42; P=0.0001) of 3-methyl-1-butanol release (y=Ag/hour) versus days (x) for each lure type (FIG. 1). Release rate decreased in all lures over time ($\beta_1$=−0.0429, $r^2$=0.96; $\beta_1$=−0.19367, $r^2$=0.98; and $\beta_1$=−0.34460, $r^2$=0.97 for 3-,5-, and 10-mm membrane release areas). Generally, the half life of the lures was about 16 days.

Example 5

All bioassays, using *A. suspensa*, were conducted as two-choice bioassays using about 30.2×30.2×122 cm flight tunnels (Heath et al.; Epsky et al, 1993; supra). Tests were run in a greenhouse under natural light conditions. Liquid test substrates were placed in 500 ml narrow mouth flasks. Solid test substrates were placed in 1.9 liter wide mouth plastic jars (Anchor Hocking, St. Paul, Minn.). Test substrates were vented into the tunnels for at least about 1 hour before the addition of flies to allow the release of volatiles to stabilize. New plastic jars were used for each change in test substrate, unless a higher concentration of the same substrate was used in subsequent bioassays. Two horizontally-mounted traps (140 ml clear plastic vial, BioQuip, Gardena, Califormia) were suspended upwind inside the tunnel (Heath et al, 1993 supra). About a 6.5×6.5 cm piece of fluorescent orange adhesive paper, supplied by the Atlantic Paste and Glue Co., Inc. (Brooklyn, N.Y.), was attached to the outside face of the trap with double sided tape. This provided a visual cue (Greany et al., Entomol. Exp. Appl., Volume 21, 63–70, 1977; Sivinski Florida Entomol., Volume 73, 123–128, 1990) and a sticky surface to capture responding flies. Test substrate volatiles were introduced into the tunnel through the trap, and the trap face and the adhesive paper had about 1.5 cm holes in the center to allow point source release of test substrate volatiles. The positions of the two test substrates offered in a bioassay were switched after each test to reduce position effects. Twenty females were released at the downwind end of the tunnel and the number of flies captured on the adhesive paper trap face was recorded after approximately 20 hours. Flies were given water, but no food, during a bioassay.

In the first experiment, about 1.7 and 17 ml of washed cells in about 99.3 and 83 ml of tap water, respectively, were tested against a blank (about 100 ml of tap water). The washed cells were added to water to prevent desiccation of the sample during the bioassay. The experiment was replicated eight times. The second experiment was conducted to confirm the biological activity of 3-methyl-1-butanol and to determine the concentration of 3-methyl-1-butanol emitted from the washed cell preparation. Females were given the choice of about 13 ml of washed cells in about 87 ml of tap water and a low dose of 3-methyl-1-butanol lure at one of three release rates: a)lure with about a 3 mm membrane release area and loaded with about 5 μl of 3-methyl-1-butanol and b) one or two lures with about a 3 mm membrane release area and loaded with about 10 μl of 3-methyl-1-butanol. Each comparison was replicated six times. In subsequent testing, flies were then given the choice of volatiles from *E. agglomerans*-inoculated and sterile TSA plates. Initial tests confirmed that volatiles from *E. agglomerans*-inoculated TSA plates captured more females than uninoculated plates. However, it was found that there was a large amount of variation in chemical release among the inoculated TSA plates and that the inoculated TSA plates also released a large amount of ammonia, which is known to be attractive to fruit flies, in comparison with sterile TSA plates tests (results below). Therefore the third experiment used synthetic lures in place of *E. agglomerans*-inoculated plates to standardize release rates and was designed to compare attraction due to ammonia with attraction due to 3-methyl-1-butanol. Females were given the choice of an ammonia lure or a 3-methyl-1-butanol lure loaded with about 100 μl of 3-methyl-1-butanol with either about a 3-,5-, or 10-mm membrane release area. The test was replicated four times. The fourth experiment was conducted to determine if the combination of ammonia and 3-methyl-1-butanol was more attractive than ammonia alone. The test was five times and used the same lure formulations as were used in experiment three. Two sample t-tests using Proc TTEST (SAS Institute, 1985, supra) were used for comparisons between the two choices offered together.

More flies were captured in response to the about 17 ml of washed cells than to a water blank, although there was no difference when the about 1.7 ml of washed cells were tested (Table 1 below). The 3-methyl-1-butanol lures that released about 0.187 μg/hour captured as many flies as washed cells (Table 1), confirming the biological activity of 3-methyl-1-butanol and indicating the approximate release rate from this concentration of washed cells. Overall capture of flies in these tests, however, was very low and only half of the flies were captured in any of the bioassays. Therefore, tests were continued with higher release rates of 3-methyl-1-butanol and the lures were formulated to mimic release from *E. agglomerans*-inoculated TSA plate at the lowest concentration (i.e., lure with about a 3-mm membrane release area loaded with about 50 μl 3-methyl-1-butanol), and at about 5-fold and 10-fold higher concentrations (i.e., lures with about 5- and 10-mm membrane release areas, respectively, loaded with about 50 μl 3-methyl-1-butanol). In experiment three, the three concentrations of 3-methyl-1-butanol were tested against about 100 μl/hour ammonia, which has been found to be an optimal concentration for tests in the bioassay system. The 3-methyl-1-butanol at the two lower release rates captured fewer females than the ammonia, but 3-methyl-1-butanol at the highest release rate tested captured as many flies as ammonia (Table 2, below). When tested in combination with ammonia in experiment four, the highest concentration of 3-methyl-1-butanol combined with ammonia captured more females than the ammonia alone (Table 3). In bioassays in which both ammonia and the highest dose 3-methyl-1-butanol lure were offered either alone (experiment 3) or in combination (experiment 4), an average of 18 out of the 20 flies in the bioassay were captured.

TABLE 1

RESULTS OF TWO-CHOICE BIOASSAY TESTS OF RESPONSE (MEAN ± SD) OF 20 FEMALE *A. SUSPENSA* PER TEST TO VOLATILES FROM WASHED *E. Agglomerans* CELLS VERSUS A BLANK (EXPERIMENT 1) OR SEVERAL CONCENTRATIONS OF 3-METHYL-1-BUTANOL SYNTHETIC LURES (EXPERIMENT 2)

| Choice 1 | | Choice 2 | | | | |
| --- | --- | --- | --- | --- | --- | --- |
| Treatment | Response | Treatment | Response | t | df | P |
| Experiment 1 | | | | | | |
| 1.7 ml cells | 4.6 ± 3.58 | water blank | 4.7 ± 1.67 | 0.0894 | 14 | ns* |
| 17 ml cells | 8.1 ± 3.09 | water blank | 2.0 ± 1.51 | 5.0349 | 14 | 0.0002 |

TABLE 1-continued

RESULTS OF TWO-CHOICE BIOASSAY TESTS OF RESPONSE
(MEAN ± SD) OF 20 FEMALE A. SUSPENSA PER TEST TO
VOLATILES FROM WASHED E. Agglomerans CELLS VERSUS
A BLANK (EXPERIMENT 1) OR SEVERAL CONCENTRATIONS OF
3-METHYL-1-BUTANOL SYNTHETIC LURES (EXPERIMENT 2)

| Choice 1 | | Choice 2 | | | | |
|---|---|---|---|---|---|---|
| Treatment | Response | Treatment | Response | t | df | P |
| Experiment 2 | | | | | | |
| 13 ml cells | 4.8 ± 1.83 | 0.046 µg/h lure | 1.3 ± 1.21 | 3.8996 | 10 | 0.0030 |
| 13 ml cells | 5.8 ± 2.92 | 0.082 µg/h lure | 2.2 ± 5.83 | 2.0117 | 10 | 0.0720 |
| 13 ml cells | 6.7 ± 3.50 | 0.187 µg/h lure | 3.3 ± 3.56 | 1.6352 | 10 | ns |

*not significant

TABLE 2

RESULTS OF TWO-CHOICE BIOASSAY TESTS (EXPERIMENT 3)
OF RESPONSE (MEAN ± SD) OF 20 FEMALE A. suspensa
PER TEST TO VOLATILES FROM SEVERAL CONCENTRATIONS
OF 3-METHYL-1-BUTANOL SYNTHETIC LURES (AVERAGE
RELEASE RATE) VERSUS AMMONIA (100 µg/h)

| Choice 1 | | Choice 2 | | | | |
|---|---|---|---|---|---|---|
| Treatment | Response | Treatment | Response | t | df | P |
| 1.23 µg/h lure | 5.0 ± 2.16 | ammonia | 11.5 ± 3.70 | 3.0361 | 6 | 0.0229 |
| 5.44 µg/h lure | 5.3 ± 1.70 | ammonia | 12.3 ± 4.19 | 3.0921 | 6 | 0.0213 |
| 12.16 µg/h lure | 9.0 ± 2.16 | ammonia | 9.3 ± 3.86 | 0.1130 | 6 | ns* |

*not significant

TABLE 3

RESULTS OF TWO-CHOICE BIOASSAY TESTS (EXPERIMENT 4)
OF RESPONSE (MEAN ± SD) OF 20 FEMALE A. suspensa
PER TEST TO VOLATILES FROM SEVERAL CONCENTRATIONS
(AVERAGE RELEASE RATE) OF 3-METHYL-1-BUTANOL
SYNTHETIC LURES PLUS AMMONIA VERSUS AMMONIA ALONE.
A 100 µg/h AMMONIA RELEASE RATE WAS USED IN ALL TESTS.

| Choice 1 | | Choice 2 | | | | |
|---|---|---|---|---|---|---|
| Treatment | Response | Treatment | Response | t | df | P |
| 1.23 µg/h lure + ammonia | 8.6 ± 4.15 | ammonia | 9.2 ± 2.17 | 0.2860 | 8 | ns* |
| 5.44 µg/h lure + ammonia | 8.6 ± 4.03 | ammonia | 8.8 ± 1.30 | 0.1054 | 8 | ns |
| 12.16 µg/h lure + ammonia | 11.6 ± 2.41 | ammonia | 7.0 ± 3.31 | 2.5095 | 8 | 0.0364 |

*not significant

Example 6

To test the effect of the addition of 3-methyl-1-butanol to ammonium acetate and putrescine on the capture of *Anastrepha ludens* under field conditions, cylindrical traps prepared from a commercially produced adhesive paper were used. The adhesive paper traps were prepared as described previously (Heath et al., supra). Traps were made from light fluorescent green adhesive paper supplies by the Atlantic Paste and Glue Co., Inc. (Brooklyn, N.Y.). Preliminary field cage tests conducted in Guatemala with fruit-reared *A. ludens* indicated that two 3-methyl-1-butanol lures were needed per trap. Each lure with about a 10-mm diameter circle release area, as described above, especially in examples 4 and 5, was loaded with 50 A1 of 3-methyl-1-butanol. Therefore, synthetic bait treatments were a)two 3-methyl-1-butanol lures, b) one ammonium acetate lure and one putrescine lure, and c) the combination of two 3-methyl-1-butanol lures, one ammonium acetate lure and one putrescine lure. 3-methyl-1-butanol lures were replaced every two weeks, ammonium acetate and putrescine lures were replaced after the first six weeks. Liquid protein-baited McPhail traps were included in the test because they are the standard trap for *A. ludens* (Gilbert et al., 1984, supra). McPhail traps were baited with three torula yeast-borax pellets (ERA Int., Freeport, N.Y.) in about 300 ml of water.

Field trials were conducted in Finca Lucky in a mixed planting of coffee and citrus, located near Palin, Guatemala. The experimental design was a Latin square of a four line by four trap position trapping grid. The traps were placed approximately 10 meters apart along a line and there were four lines of traps with two lines of trees without traps between each baited line. All females captured per bait were pooled and were placed in about 70% isopropanol. Subsamples of up to 10 females were dissected, egg load determined from number of mature eggs in the ovary, and mating status determined from presence or absence of sperm in the spermathecae. Traps were moved sequentially within a line at time of sampling. The orange trees were in fruit, but most of the fruit were immature and not suitable for *A. ludens* oviposition or larval development at the start of the study period. However, fruit matured and became available for oviposition throughout the study. Due to the low population level of *A. ludens* during this study, the entire trapping grid was moved within the Finca about every 3–4 weeks. Traps were checked about every 2–3 days, numbers of female and male *A. ludens* were recorded, and the total number of flies trapped per treatment was summed by sex collected each sample period. Adhesive paper trap bodies were replaced at each sample period and the McPhail traps were baited with fresh torula yeast solution every other week. The torula yeast solution was recycled the other sample times, and water was added to bring the liquid level back to about 300 ml if needed. Tests were conducted for about a 10 week period for a total of 20 consecutive replicates.

Sum totals were converted to percentage per treatment per sample date for statistical analysis to facilitate comparisons among the range of fruit fly population densities sampled. Data were assessed by the Box-Cox procedure (Box et al, Statistics for Experimenters. An Introduction to Design, Data Analysis, and Model Building. J. Wiley and Sons, New York, New York, 1978) and were square root transformed (x+0.5) to stabilize the variance before analysis. Data were analyzed by one-way analysis of variance using Proc GLM (supra) followed by least significant difference test (LSD, P=0.05) for mean separation.

Figure 2:
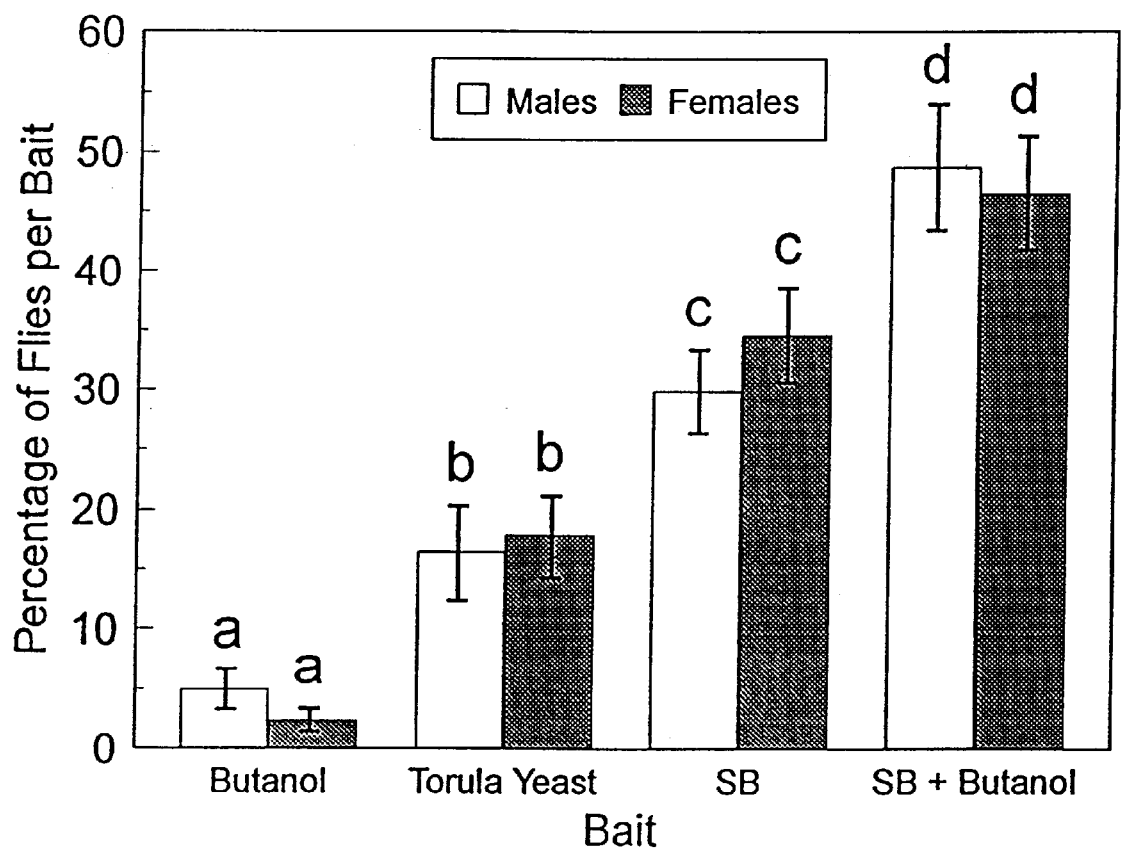
FIG. 2 is a graph showing relative trap efficiency as indicated by the average percentage (±Std. error) of *A. ludens* males (solid bars) and females (crosshatch bars) captured in sticky paper cylindrical traps baited with either 3-methyl-1-butanol (butanol), ammonium acetate and putrescine (SB), or ammonium acetate, putrescine and 3-methyl-1-butanol (SB+Butanol), or in McPhail traps baited with torula yeast in field trails conducted in Palin, Guatemala. Bars headed by the same letter within a sex are not significantly different (LSD mean separation test on square root [x+0.5] transformed data, P=0.05; non-transformed means presented).

A total of 1301 *A. ludens* were captured over the 10 weeks of field test, with approximately 4 males and approximately 5 females captured per trap per week. Bait treatment affected capture of males (F=28.60; df=3,76; P=0.0001) and females (F=45.23; df=3,76; P=0.0001). Traps baited with ammonium acetate, putrescine, and 3-methyl-1-butanol captured the greatest percentage of both males and females (FIG. 2). Traps baited with the 3-methyl-1-butanol lure alone captured the least.

Figure 3:
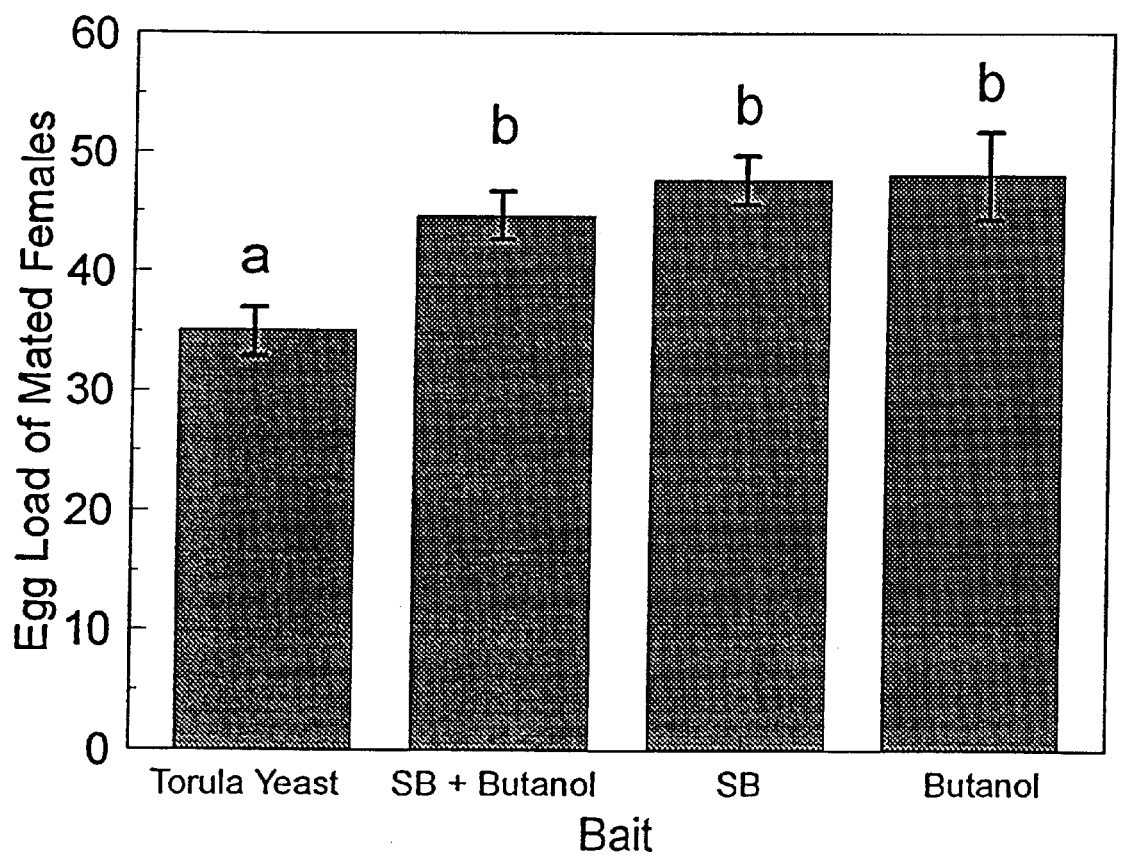
FIG. 3 is a graph showing average egg load (±std. error) of mated female *A. ludens* captured in sticky paper cylindrical traps baited with 3-methyl-1-butanol (butanol), ammonium acetate and putrescine (SB), or ammonium acetate, putrescine and 3-methyl-1-butanol (SB+Butanol), and McPhail traps baited with torula yeast in field trials conducted in Palin, Guatemala. Bars headed by the same letter within a sex are not significantly different (LSD mean separation test, P=0.05).
Figure 4:
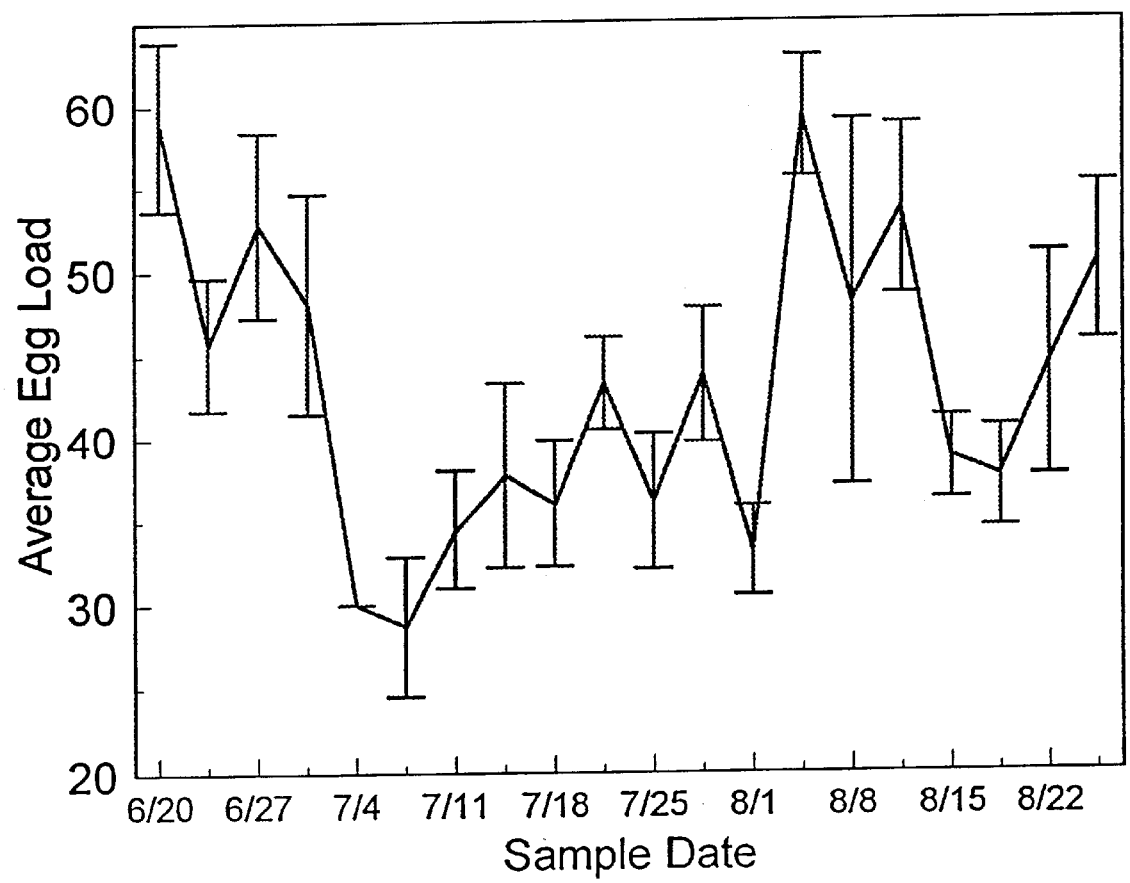
FIG. 4 is a graph showing average egg load (±std. error) of all mated female *A. ludens* captured per sample date over the time period of the field trials conducted in Palin, Guatemala. Number of females dissected per sample date depended on availability, and ranged from 1 to 24.

Most of the females captured throughout the study were mated, as indicated by presence of sperm in the spermathecae. Of the 140 dissected females from traps baited with ammonium acetate and putrescine, 99(71%) were mated. Of the 155 dissected females from traps baited with ammonium acetate, putrescine, and 3-methyl-1-butanol, 123 (83%) were mated. Only 14 females were available from traps baited with 3-methyl-1-butanol alone, but 13 (93%) were mated. Among the 81 unmated females dissected, 11 had mature eggs, and egg load ranged from 2 to 20. Among all mated females captured, egg loads ranged from 1–119 and only one female had no mature eggs. Females captured on sticky traps baited with any of the synthetic lures had greater egg loads than females captured in McPhail traps baited with protein solution (F=6.44; df=3,310; P=0.0003; FIG. 3). Over the 10 weeks of the study, average egg load among all mated females captured ranged from 28.7 (±15.09) during the 6th sample period to 59.3(±10.89) during the 14th sample period (FIG. 4).

Based on the data obtained, 3-methyl-1-butanol is synergistic in attraction of *A. ludens* when used in combination with the previously published food-based synthetic attractant consisting of ammonia, acetic acid, and putrescine. Few flies were captured in traps baited with 3-methyl-1-butanol alone.

Comparison of egg load over time indicated that a decrease in average egg load occurred between the fourth and fifth sample period, and the egg load remained lower through the thirteenth sample period. This may indicate that fruit became suitable for oviposition during this time period. There was no indication of appearance of newly emerged adults, as few unmated females were captured and the percent mated remained fairly constant throughout the study. There tended to be more mated *A. ludens* females in synthetic lure-baited traps than liquid protein-baited McPhail traps, and the highest percentage was captured in traps baited with 3-methyl-1-butanol alone.

The forgoing description is for the purpose of illustration. Others skilled in the art can apply the knowledge described to other frugivorous pest insects. Such detail is solely for that purpose and those skilled in the art can make variations therein without departing from the spirit and scope of the invention.

We claim:

1. An attractant composition for frugivorous pest insects consisting essentially of a vapor blend of
   (a) ammonia, and
   (b) a synergistic amount of a vapor of 3-alkyl-1-butanol, wherein said composition provides an effective frugivorous pest insect attractant amount of said vapor blend.

2. The composition of claim 1 wherein said 3-alkyl-1-butanol is 3-methyl-1-butanol.

3. The composition of claim 1 wherein said ammonia is provided by ammonium carbonate, ammonium bicarbonate or ammonium acetate.

4. An attractant composition for frugivorous pest insects consisting essentially of a vapor blend of
   (a) a vapor selected from the group consisting of ammonia, acetic acid, putrescine, and mixtures thereof; and
   (b) a synergistic amount of a 3-alkyl-1-butanol; wherein said composition provides an effective frugivorous pest insect attractant amount of said vapor blend.

5. An attractant composition for frugivorous pest insects comprising a vapor blend consisting of ammonia, acetic acid, putrescine, and 3-methyl-1-butanol wherein said composition provides effective frugivorous pest insect attractant amounts of said vapor blend.

6. The composition of claim 5 wherein said 3-alkyl-1-butanol is 3-methyl-1-butanol.

7. A trapping system for monitoring and/or controlling frugivorous pest insects comprising
   a trapping means, and
   an attractant consisting essentially of in a dispensing means comprising a vapor blend of
   (a) ammonia, and
   (b) a synergistic amount of a vapor of 3-alkyl-1-butanol, wherein said composition provides an effective frugivorous pest insect attractant amount of said vapor blend.

8. The composition of claim 5 wherein said ammonia is provided by ammonium carbonate, ammonium bicarbonate or ammonium acetate; and said acetic acid is provided by aqueous acetic acid, concentrated acetic acid or ammonium acetate.

9. The composition of claim 5 wherein said ammonia vapor and said acetic acid vapor are provided by ammonium acetate in a dispensing means, said putrescine vapor is provided by liquid putrescine in a dispensing means, and said 3-methyl-1-butanol vapor is provided by liquid 3-methyl-1-butanol in a dispensing means.

10. A lure for attracting frugivorous pest insects which consists essentially of a vapor blend of a vapor selected from the group consisting of ammonia, acetic acid, and putrescine and mixtures thereof; and a 3-alkyl-1-butanol; wherein said compounds are contained in dispensing means.

11. A trapping system for monitoring and/or controlling frugivorous pest insects comprising
    a trapping means,
    a dispensing means located in said trapping means which contains and dispenses an attractant vapor blend consisting essentially of of
    (a) a vapor selected from the group consisting of ammonia, acetic acid, putrescine, and mixtures thereof; and
    (b) a synergistic amount of a 3-alkyl-1-butanol; wherein said composition provides an effective frugivorous pest insect attractant amount of said vapor blend.

12. A method for attracting frugivorous pest insects comprising
    providing an attractant composition consisting essentially of a vapor blend of
    (a) a vapor selected from the group consisting of ammonia, acetic acid, putrescine and mixtures thereof; and
    (b) a synergistic amount of a 3-alkyl-1-butanol;
    wherein said vapor blend is in effective frugivorous pest insect attractant amounts.

13. The system of claim 11 wherein said 3-alkyl-1-butanol is 3-methyl-1-butanol.

14. A method for attracting frugivorous pest insects comprising placing in an area where said insects are to be attracted a trapping means containing dispensing means located in said trapping means which contains and dispenses an attractant vapor blend consisting essentially of of
    (a) a vapor selected from the group consisting of ammonia, acetic acid, putrescine, and mixtures thereof; and
    (b) a synergistic amount of a 3-alkyl-1-butanol; wherein said composition provides an effective frugivorous pest insect attractant amount of said vapor.

15. A method for attracting frugivorous pest insects comprising providing an attractant composition which provides a vapor blend consisting essentially of
    (1) a vapor selected from the group consisting of ammonia, acetic acid, putrescine and mixtures thereof; and
    (2) A synergistic amount of a 3-alkyl-1-butanol; wherein said composition provides an effective attractant amount of said vapor blend.

16. The method of claim 12 wherein said 3-alkyl-1-butanol is 3-methyl-1-butanol.

* * * * *

UNITED STATES PATENT AND TRADEMARK OFFICE
CERTIFICATE OF CORRECTION

PATENT NO.   : 6,224,890 B1
DATED        : May 1, 2001
INVENTOR(S)  : Heath et al.

It is certified that error appears in the above-identified patent and that said Letters Patent is hereby corrected as shown below:

Claim 7,
Line 4 and 5 reads -- an attractant consisting essentially of in a dispensing means comprising a vapor blend of
Please add -- composition in a dispensing means consisting essentially of -- after the word attractant and before the word consisting on line 4.
Please delete the words -- consisting essentially of in a dispensing means comprising -- on lines 4 and 5.

Claim 11,
Line 5 reads -- contains and dispenses an attractant vapor blend con --
Please add the word composition after the word blend and before the word con --

Claim 14,
Line 5 reads -- an attractant vapor blend consisting essentially of of
Please add the word composition after blend and before consisting.
Please delete one of the words of, for it was repeated.

Signed and Sealed this

Twenty-fifth Day of September, 2001

Attest:

NICHOLAS P. GODICI
Attesting Officer   Acting Director of the United States Patent and Trademark Office